United States Patent [19]
Burr et al.

[11] Patent Number: 5,919,648
[45] Date of Patent: Jul. 6, 1999

[54] INDUSTRIAL ENZYMES

[75] Inventors: Keith William Burr; Martin Ramsden, both of Ulverston; Graham Timothy Illing, Montrose; Leslie Ann Harrison, Ulverston; Nicholas John Maishman, Beckenham; David Wilson Spence; Andrew Slade, both of Ulverston, all of United Kingdom

[73] Assignee: Glaxo Group Limited, Greenford, United Kingdom

[21] Appl. No.: 08/817,900

[22] PCT Filed: Nov. 15, 1995

[86] PCT No.: PCT/EP95/04487

§ 371 Date: Apr. 25, 1997

§ 102(e) Date: Apr. 25, 1997

[87] PCT Pub. No.: WO96/16174

PCT Pub. Date: May 30, 1996

[30] Foreign Application Priority Data

Nov. 17, 1994 [GB] United Kingdom .................... 9423212

[51] Int. Cl.$^6$ ............... C12P 35/00; C12N 9/14; C12N 1/20; C12N 15/00

[52] U.S. Cl. ................. 435/47; 435/195; 435/252.33; 435/320.1; 435/874; 435/69.1; 536/23.2

[58] Field of Search ............... 435/47, 195, 69.1, 435/71.2, 252.3, 252.33, 320.1, 874; 536/23.2

[56] References Cited

U.S. PATENT DOCUMENTS 5,320,948   6/1994   Iwami et al. ........................... 435/47

*Primary Examiner*—Charles L. Patterson, Jr.
*Assistant Examiner*—Tekchand Saidha
*Attorney, Agent, or Firm*—Nixon & Vanderhye P.C.

[57] ABSTRACT

The present invention relates to an enzyme process for the one-step conversion of cephalosporin C or a derivative thereof into 7-aminocephalosporanic acid or a corresponding derivative thereof. The one step conversion is effected using a cephalosphorin C amidohydrolase derived from *Pseudomonas Vesicularis* B965, or from any cephalosporin C amidolydrolase producing or potentially producing descendants thereof, or from expression of DNA derived from *Pseudomonas Vesicularis* B965 or any cephalosporin C amidohydrolase producing or potentially producing descendants thereof

8 Claims, 1 Drawing Sheet

Fig. 1

RESTRICTION MAPS OF THE CLONED
P. VESICULARIS REGIONS OF VARIOUS PLASMIDS (a) pVS42
(b) pVS44
(c) pVS4461/pTT1861

SCALE BAR IN kb

| B | BamHI | S | SmaI |
| H | HindIII | Sl | SalI |
| K | KpnI | Sp | SphI |
| P | PstI | X | XhoI |

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2391 base pairs
      (B) TYPE: nucleic acid
      (C) STRANDEDNESS: double
      (D) TOPOLOGY: linear    (ix) FEATURE:
      (A) NAME/KEY: CDS
      (B) LOCATION:1..2388

(xi) SEQUENCE DESCRIPTION: SEQ ID NO: 1:

```
ATG GAC GGC CCG CCG CCG AGG GGG TTA GCC TGT GGC GGG ACC CAC GAC        48
Met Asp Gly Pro Pro Pro Arg Gly Leu Ala Cys Gly Gly Thr His Asp
 1               5                  10                  15

GAA AGG ATA GCA ATG CTC GAC CGG CGC CTA TTT CTG CTT GGT TCG GCG        96
Glu Arg Ile Ala Met Leu Asp Arg Arg Leu Phe Leu Leu Gly Ser Ala
             20                  25                  30

GCG ACC GTG CTG GTG TCT GCC GCC TGC CAC GGC CAG TCG GTA CCG GCG       144
Ala Thr Val Leu Val Ser Ala Ala Cys His Gly Gln Ser Val Pro Ala
         35                  40                  45

ACA GCA CCG ACC CGC GTG GCG GGG CTT TCG GCA CCG ATC GAG ATC ATC       192
Thr Ala Pro Thr Arg Val Ala Gly Leu Ser Ala Pro Ile Glu Ile Ile
     50                  55                  60

GAC GAT CGC TGG GGC GTG CCG CAT ATC CGC GCG CAG ACG AAG GCG GAT       240
Asp Asp Arg Trp Gly Val Pro His Ile Arg Ala Gln Thr Lys Ala Asp
 65                  70                  75                  80

GCG TTT TTC GGA CAG GGC TAT GTC GTG GCG CGC GAC CGA CTG TTC CAG       288
Ala Phe Phe Gly Gln Gly Tyr Val Val Ala Arg Asp Arg Leu Phe Gln
                 85                  90                  95

ATC GAC CTG GCG CAT CGC CGC GAA CTG GGC CGG ATG GCG GAA GCG TTC       336
Ile Asp Leu Ala His Arg Arg Glu Leu Gly Arg Met Ala Glu Ala Phe
            100                 105                 110

GGG CCG GAT TTT GCC AAG CAT GAT GCC GTC GCC CGA CTG TTC CAT TAT       384
Gly Pro Asp Phe Ala Lys His Asp Ala Val Ala Arg Leu Phe His Tyr
        115                 120                 125

CGC GGC GAC CTG GAC GCC GAG CTG GCG CGC GTA CCC AAG GAA GTT CGC       432
Arg Gly Asp Leu Asp Ala Glu Leu Ala Arg Val Pro Lys Glu Val Arg
    130                 135                 140

GAC TGC GTG GCC GGA TAT GTC GCA GGC ATC AAT GCG CGG ATC GCC GAG       480
Asp Cys Val Ala Gly Tyr Val Ala Gly Ile Asn Ala Arg Ile Ala Glu
145                 150                 155                 160

GTC GAG AAG GAC CCG AGC CTA TTG CCG CCG GAA TAT CGC ATC CTG GGG       528
Val Glu Lys Asp Pro Ser Leu Leu Pro Pro Glu Tyr Arg Ile Leu Gly
```

```
                        165                 170                 175
GTG ACG CCG CTG CGC TGG GAC ATC CGC GAT CTG GTG CGC GCG CGG GGC          576
Val Thr Pro Leu Arg Trp Asp Ile Arg Asp Leu Val Arg Ala Arg Gly
        180                 185                 190

AGC TCA ATC GGC AAT GCC GAC GAC GAG ATC CGC CGT GCG AAA CTG GCC          624
Ser Ser Ile Gly Asn Ala Asp Asp Glu Ile Arg Arg Ala Lys Leu Ala
        195                 200                 205

GCG CTC GGC ATG CTG GAG CTG GAC GCG GTG ATC GCG CCG CTG CGG CCG          672
Ala Leu Gly Met Leu Glu Leu Asp Ala Val Ile Ala Pro Leu Arg Pro
        210                 215                 220

ACG TGG AAG CTG GCC GTG CCG GAG GGG CTG GAC CCG TCA AAG GTG AGT          720
Thr Trp Lys Leu Ala Val Pro Glu Gly Leu Asp Pro Ser Lys Val Ser
225                 230                 235                 240

GAT GCG GAT CTG GGC GTG CTT CAG CTG GGA CGG CTG CCG TTC GGA CCC          768
Asp Ala Asp Leu Gly Val Leu Gln Leu Gly Arg Leu Pro Phe Gly Pro
                245                 250                 255

GAC ACG CCG ACG CGT GAG CCA GAA GAG GAT CTG GAC CGC GCG CAG GCG          816
Asp Thr Pro Thr Arg Glu Pro Glu Glu Asp Leu Asp Arg Ala Gln Ala
            260                 265                 270

GGG TCG AAC GCC TGG ACC GTC GCT GGC AGC CGC ACC AGC ACT GGC CGC          864
Gly Ser Asn Ala Trp Thr Val Ala Gly Ser Arg Thr Ser Thr Gly Arg
        275                 280                 285

CCC ATT CTG GCC AAT GAT CCG CAT CTG GGG ATC GGC GGG TTC GGG CCG          912
Pro Ile Leu Ala Asn Asp Pro His Leu Gly Ile Gly Gly Phe Gly Pro
        290                 295                 300

CGA CAT GTG GCG CAT CTG ACC GCG CCG GGT CTC GAC GTG ATT GGC GGT          960
Arg His Val Ala His Leu Thr Ala Pro Gly Leu Asp Val Ile Gly Gly
305                 310                 315                 320

GGC GCG CCT GGA CTG CCC GGC ATC ATG CAG GGG CAT ACC GAC CGT TTC          1008
Gly Ala Pro Gly Leu Pro Gly Ile Met Gln Gly His Thr Asp Arg Phe
                325                 330                 335

GCC TTT GGC CGG ACC AAT TTC CAT ATC GAC CAG CAG GAT CTG TTC GTC          1056
Ala Phe Gly Arg Thr Asn Phe His Ile Asp Gln Gln Asp Leu Phe Val
            340                 345                 350

CTG GAG CTG GAT CCC AAC GAT CCC GAG CGG TAC CGC CAC GAC GGC GGC          1104
Leu Glu Leu Asp Pro Asn Asp Pro Glu Arg Tyr Arg His Asp Gly Gly
        355                 360                 365

TGG AAG CGG TTC GAG CGG GTG GAG GAG ACG ATC CCG GTC AAG GAC GGT          1152
Trp Lys Arg Phe Glu Arg Val Glu Glu Thr Ile Pro Val Lys Asp Gly
        370                 375                 380

CCG CCG CAG AAG GTG GTC CTG CGC TAC GCG GTA CAG GGC CCG GTG ATC          1200
Pro Pro Gln Lys Val Val Leu Arg Tyr Ala Val Gln Gly Pro Val Ile
385                 390                 395                 400

ATG CAC GAT CCG GCG GCG CGC CGG GCG ACG GTG CTC GGG TCG ATC GGG          1248
Met His Asp Pro Ala Ala Arg Arg Ala Thr Val Leu Gly Ser Ile Gly
                405                 410                 415

ATG CAG CCC GGC GGG TTC GGA TCG TTC GCG ATG GTG GCG ATC AAC CTG          1296
Met Gln Pro Gly Gly Phe Gly Ser Phe Ala Met Val Ala Ile Asn Leu
            420                 425                 430

TCG CGC GAC TGG AAC AGC CTG AAG GAA GCG TTC AAG CTG CAC CCG TCG          1344
Ser Arg Asp Trp Asn Ser Leu Lys Glu Ala Phe Lys Leu His Pro Ser
        435                 440                 445

CCC ACC AAC CTG CAT TAT GCC GAC GTT GAC GGG AAC CAC GGC TGG CAA          1392
Pro Thr Asn Leu His Tyr Ala Asp Val Asp Gly Asn His Gly Trp Gln
        450                 455                 460

GTG ATC GGC TTC GTT CCG CAG CGC AAG AAG GGC GAC GGG CTG ATG CCG          1440
Val Ile Gly Phe Val Pro Gln Arg Lys Lys Gly Asp Gly Leu Met Pro
465                 470                 475                 480

GTG CCG GGC GAC GGG CGC TAC GAC TGG AAC AGC TAT CGC GAT TTC CGC          1488
Val Pro Gly Asp Gly Arg Tyr Asp Trp Asn Ser Tyr Arg Asp Phe Arg
```

```
                        485                 490                 495
GTG CTG CCG AGC GAG TTC AAC CCG TCC AAG GGC TGG TTC GCA TCT GCC    1536
Val Leu Pro Ser Glu Phe Asn Pro Ser Lys Gly Trp Phe Ala Ser Ala
            500                 505                 510

AAC CAG AAC AAC CTG CCG GCG AAT TGG CCG CGC GAT CGC ATT CCG GCG    1584
Asn Gln Asn Asn Leu Pro Ala Asn Trp Pro Arg Asp Arg Ile Pro Ala
            515                 520                 525

TTC TCG TTC CGC GAC CCT TAT CGT TAC GAG CGC GTC GCC GAG GTG CTG    1632
Phe Ser Phe Arg Asp Pro Tyr Arg Tyr Glu Arg Val Ala Glu Val Leu
            530                 535                 540

GCA TCG CAG CCG CGC CAT TCG GTG GCG GAC AGC GTG GCA TTG CAG TTC    1680
Ala Ser Gln Pro Arg His Ser Val Ala Asp Ser Val Ala Leu Gln Phe
545                 550                 555                 560

GAC ACG CTG TCG ACG CCG GCC AAG CAG TTC CTG GCG TTG CTA CCC AAG    1728
Asp Thr Leu Ser Thr Pro Ala Lys Gln Phe Leu Ala Leu Leu Pro Lys
            565                 570                 575

CAG CCG TCC GCG GGT GCG GCC CCG GCG GTG AAG ATG CTG TCG GGG TGG    1776
Gln Pro Ser Ala Gly Ala Ala Pro Ala Val Lys Met Leu Ser Gly Trp
            580                 585                 590

GAC GCG AAG CTG GAC AAG GAT AGC GGC GCG GCG GCG CTG TAC GAG ATC    1824
Asp Ala Lys Leu Asp Lys Asp Ser Gly Ala Ala Ala Leu Tyr Glu Ile
            595                 600                 605

GTG TGG CGT GAC CTG GGC AAG CGG ATG CTG GCG GCC ATC GTG CCG GAG    1872
Val Trp Arg Asp Leu Gly Lys Arg Met Leu Ala Ala Ile Val Pro Glu
            610                 615                 620

CAG GCG AAG GAG CTG GTG GAC GAG ATC GCA CCA TCC GAG CTG CTG CGC    1920
Gln Ala Lys Glu Leu Val Asp Glu Ile Ala Pro Ser Glu Leu Leu Arg
625                 630                 635                 640

CGT GCG GCA AGC CGG CCG GCG ATG GTG GAC GAG GCG CTG GCG AGC GGC    1968
Arg Ala Ala Ser Arg Pro Ala Met Val Asp Glu Ala Leu Ala Ser Gly
            645                 650                 655

TGG GCC GAG GCG CAG CGA CTG ATG GGC AGC GAT CCA TCA GCC TGG CGC    2016
Trp Ala Glu Ala Gln Arg Leu Met Gly Ser Asp Pro Ser Ala Trp Arg
            660                 665                 670

TGG GGC ACG TTG CAC CAG GTG CGG ATC GCG CAT CCG CTG TCG AGC ATC    2064
Trp Gly Thr Leu His Gln Val Arg Ile Ala His Pro Leu Ser Ser Ile
            675                 680                 685

CCG GCC ATC GCC GCG GCG TTC CCC CCG ATT GAG GGC GAG GGA TCG GGC    2112
Pro Ala Ile Ala Ala Ala Phe Pro Pro Ile Glu Gly Glu Gly Ser Gly
            690                 695                 700

GGC GAC AGC TAT ACC GTC ATG GCG CGT TGG CTG GGC AAT GGC CCG GGC    2160
Gly Asp Ser Tyr Thr Val Met Ala Arg Trp Leu Gly Asn Gly Pro Gly
705                 710                 715                 720

TGG CGC ACC GGC GGC GGG GCG AGC TAC CTG CAT GTG ATC GAC GTG GGC    2208
Trp Arg Thr Gly Gly Gly Ala Ser Tyr Leu His Val Ile Asp Val Gly
            725                 730                 735

GAC TGG GAC AAA TCG GTG ATG CTG AAC CTG CCG GGG CAG TCG AAC GAC    2256
Asp Trp Asp Lys Ser Val Met Leu Asn Leu Pro Gly Gln Ser Asn Asp
            740                 745                 750

CCG CGC TCG CCG CAT TAC CGC GAT CAA TAT GCG CCG TGG ATC AAG GGC    2304
Pro Arg Ser Pro His Tyr Arg Asp Gln Tyr Ala Pro Trp Ile Lys Gly
            755                 760                 765

GAA ATG CAG CCG ATG CCG TTC AGC CGC GCC GCG GTG GAC GGT GGC GTC    2352
Glu Met Gln Pro Met Pro Phe Ser Arg Ala Ala Val Asp Gly Gly Val
            770                 775                 780

AGC CGT TCG ACG CTG ACG CCG CAG GGG AAG GGC AAG TGA                2391
Ser Arg Ser Thr Leu Thr Pro Gln Gly Lys Gly Lys
785                 790                 795

(2) INFORMATION FOR SEQ ID NO: 2:
```

(i) SEQUENCE CHARACTERISTICS:
    (A) LENGTH: 796 amino acids
    (B) TYPE: amino acid
    (D) TOPOLOGY: linear (ii) MOLECULE TYPE: protein (xi) SEQUENCE DESCRIPTION: SEQ ID NO: 2:

```
Met Asp Gly Pro Pro Arg Gly Leu Ala Cys Gly Gly Thr His Asp
 1               5                  10                  15

Glu Arg Ile Ala Met Leu Asp Arg Arg Leu Phe Leu Leu Gly Ser Ala
            20                  25                  30

Ala Thr Val Leu Val Ser Ala Ala Cys His Gly Gln Ser Val Pro Ala
            35                  40                  45

Thr Ala Pro Thr Arg Val Ala Gly Leu Ser Ala Pro Ile Glu Ile Ile
        50                  55                  60

Asp Asp Arg Trp Gly Val Pro His Ile Arg Ala Gln Thr Lys Ala Asp
 65                  70                  75                  80

Ala Phe Phe Gly Gln Gly Tyr Val Val Ala Arg Asp Arg Leu Phe Gln
            85                  90                  95

Ile Asp Leu Ala His Arg Arg Glu Leu Gly Arg Met Ala Glu Ala Phe
            100                 105                 110

Gly Pro Asp Phe Ala Lys His Asp Ala Val Ala Arg Leu Phe His Tyr
        115                 120                 125

Arg Gly Asp Leu Asp Ala Glu Leu Ala Arg Val Pro Lys Glu Val Arg
    130                 135                 140

Asp Cys Val Ala Gly Tyr Val Ala Gly Ile Asn Ala Arg Ile Ala Glu
145                 150                 155                 160

Val Glu Lys Asp Pro Ser Leu Leu Pro Pro Glu Tyr Arg Ile Leu Gly
            165                 170                 175

Val Thr Pro Leu Arg Trp Asp Ile Arg Asp Leu Val Arg Ala Arg Gly
            180                 185                 190

Ser Ser Ile Gly Asn Ala Asp Asp Glu Ile Arg Arg Ala Lys Leu Ala
        195                 200                 205

Ala Leu Gly Met Leu Glu Leu Asp Ala Val Ile Ala Pro Leu Arg Pro
    210                 215                 220

Thr Trp Lys Leu Ala Val Pro Glu Gly Leu Asp Pro Ser Lys Val Ser
225                 230                 235                 240

Asp Ala Asp Leu Gly Val Leu Gln Leu Gly Arg Leu Pro Phe Gly Pro
            245                 250                 255

Asp Thr Pro Thr Arg Glu Pro Glu Glu Asp Leu Asp Arg Ala Gln Ala
            260                 265                 270

Gly Ser Asn Ala Trp Thr Val Ala Gly Ser Arg Thr Ser Thr Gly Arg
        275                 280                 285

Pro Ile Leu Ala Asn Asp Pro His Leu Gly Ile Gly Gly Phe Gly Pro
    290                 295                 300

Arg His Val Ala His Leu Thr Ala Pro Gly Leu Asp Val Ile Gly Gly
305                 310                 315                 320

Gly Ala Pro Gly Leu Pro Gly Ile Met Gln Gly His Thr Asp Arg Phe
            325                 330                 335

Ala Phe Gly Arg Thr Asn Phe His Ile Asp Gln Gln Asp Leu Phe Val
            340                 345                 350

Leu Glu Leu Asp Pro Asn Asp Pro Glu Arg Tyr Arg His Asp Gly Gly
        355                 360                 365

Trp Lys Arg Phe Glu Arg Val Glu Glu Thr Ile Pro Val Lys Asp Gly
```

-continued

```
              370                 375                 380
Pro Pro Gln Lys Val Val Leu Arg Tyr Ala Val Gln Gly Pro Val Ile
385                 390                 395                 400

Met His Asp Pro Ala Ala Arg Arg Ala Thr Val Leu Gly Ser Ile Gly
                405                 410                 415

Met Gln Pro Gly Gly Phe Gly Ser Phe Ala Met Val Ala Ile Asn Leu
            420                 425                 430

Ser Arg Asp Trp Asn Ser Leu Lys Glu Ala Phe Lys Leu His Pro Ser
            435                 440                 445

Pro Thr Asn Leu His Tyr Ala Asp Val Asp Gly Asn His Gly Trp Gln
450                 455                 460

Val Ile Gly Phe Val Pro Gln Arg Lys Lys Gly Asp Gly Leu Met Pro
465                 470                 475                 480

Val Pro Gly Asp Gly Arg Tyr Asp Trp Asn Ser Tyr Arg Asp Phe Arg
                485                 490                 495

Val Leu Pro Ser Glu Phe Asn Pro Ser Lys Gly Trp Phe Ala Ser Ala
            500                 505                 510

Asn Gln Asn Asn Leu Pro Ala Asn Trp Pro Arg Asp Arg Ile Pro Ala
            515                 520                 525

Phe Ser Phe Arg Asp Pro Tyr Arg Tyr Glu Arg Val Ala Glu Val Leu
530                 535                 540

Ala Ser Gln Pro Arg His Ser Val Ala Asp Ser Val Ala Leu Gln Phe
545                 550                 555                 560

Asp Thr Leu Ser Thr Pro Ala Lys Gln Phe Leu Ala Leu Leu Pro Lys
                565                 570                 575

Gln Pro Ser Ala Gly Ala Ala Pro Ala Val Lys Met Leu Ser Gly Trp
            580                 585                 590

Asp Ala Lys Leu Asp Lys Asp Ser Gly Ala Ala Leu Tyr Glu Ile
            595                 600                 605

Val Trp Arg Asp Leu Gly Lys Arg Met Leu Ala Ala Ile Val Pro Glu
            610                 615                 620

Gln Ala Lys Glu Leu Val Asp Glu Ile Ala Pro Ser Glu Leu Leu Arg
625                 630                 635                 640

Arg Ala Ala Ser Arg Pro Ala Met Val Asp Glu Ala Leu Ala Ser Gly
                645                 650                 655

Trp Ala Glu Ala Gln Arg Leu Met Gly Ser Asp Pro Ser Ala Trp Arg
            660                 665                 670

Trp Gly Thr Leu His Gln Val Arg Ile Ala His Pro Leu Ser Ser Ile
            675                 680                 685

Pro Ala Ile Ala Ala Ala Phe Pro Pro Ile Glu Gly Glu Gly Ser Gly
690                 695                 700

Gly Asp Ser Tyr Thr Val Met Ala Arg Trp Leu Gly Asn Gly Pro Gly
705                 710                 715                 720

Trp Arg Thr Gly Gly Gly Ala Ser Tyr Leu His Val Ile Asp Val Gly
                725                 730                 735

Asp Trp Asp Lys Ser Val Met Leu Asn Leu Pro Gly Gln Ser Asn Asp
            740                 745                 750

Pro Arg Ser Pro His Tyr Arg Asp Gln Tyr Ala Pro Trp Ile Lys Gly
            755                 760                 765

Glu Met Gln Pro Met Pro Phe Ser Arg Ala Ala Val Asp Gly Gly Val
770                 775                 780

Ser Arg Ser Thr Leu Thr Pro Gln Gly Lys Gly Lys
785                 790                 795
```

(2) INFORMATION FOR SEQ ID NO: 3:

(i) SEQUENCE CHARACTERISTICS:
        (A) LENGTH: 90 base pairs
        (B) TYPE: nucleic acid
        (C) STRANDEDNESS: double
        (D) TOPOLOGY: linear     (ix) FEATURE:
        (A) NAME/KEY: CDS
        (B) LOCATION:7..90

(xi) SEQUENCE DESCRIPTION: SEQ ID NO: 3:

```
ACAGCT ATG ACC ATG ATT ACG AAT TTA ATA CGA CTC ACT ATA GGG AAT        48
       Met Thr Met Ile Thr Asn Leu Ile Arg Leu Thr Ile Gly Asn
                   800             805             810

TCG AGC TCG GTA CCG GCG ACA GCA CCG ACC CGC GTG GCG GGG               90
Ser Ser Ser Val Pro Ala Thr Ala Pro Thr Arg Val Ala Gly
            815             820
```

(2) INFORMATION FOR SEQ ID NO: 4:

(i) SEQUENCE CHARACTERISTICS:
        (A) LENGTH: 28 amino acids
        (B) TYPE: amino acid
        (D) TOPOLOGY: linear     (ii) MOLECULE TYPE: protein     (xi) SEQUENCE DESCRIPTION: SEQ ID NO: 4:

```
Met Thr Met Ile Thr Asn Leu Ile Arg Leu Thr Ile Gly Asn Ser Ser
 1               5                  10                  15

Ser Val Pro Ala Thr Ala Pro Thr Arg Val Ala Gly
            20                  25
```

INDUSTRIAL ENZYMES

The present invention relates to an enzyme process for the one step conversion of cephalosporin C or a derivative thereof into 7-aminocephalosporanic acid or a corresponding derivative thereof The one step conversion is effected using a cephalosporin C amidohydrolase enzyme derived from *Pseudomonas vesicularis* B965, or from any cephalosporin C amidohydrolase producing or potentially producing descendants thereof, or from any expression of DNA, particularly a recombinant DNA molecule, derived from *Pseudomonas vesicularis* B965 as described herein, or any cephalosporin C amidohydrolase producing or potentially producing descendants thereof.

Cephalosporin C is the fermentation product of the cephalosporin biosynthesis pathway and although it has been shown to have some activity against gram-negative microorganisms as an antibiotic itself, the major commercial use of cephalosporin C is as a building block for other cephalosporin-like antibiotics. In particular, the D-α-aminoadipoyl side chain may be removed to give the highly useful intermediate 7-aminocephalosporanic acid (7-ACA) which is a precursor to a wide range of semi-synthetic cephalosporin antibiotics including cephalothin, cephaloridine and cefuroxime.

The current industrial process for producing 7-ACA from cephalosporin C is a chemical cleavage of the D-α-aminoadipoyl side chain. There are several different methods in use (see for instance A Smith in "Comprehensive Biotechnology: the Principles, Applications and Regulations of Biotechnology in Industry, Agriculture and Medicine", Volume 3 ( "The Practice of Biotechnology: Current Commodity Products"), Eds. H W Blanch et.al., esp. pp.163–185, Pergamon Press, Oxford, UK, 1985), but all are essentially imino-halide processes with appropriate protection of amino and carboxyl groups. See, for example, the nitrosyl chloride cleavage developed by Morin et al (J. Am. Chem. Soc., 84, 3400 (1962)) now superseded by the imino ether method developed by Ciba Geigy (Fechtig et al, Helv. Chim. Acta., 51, 1108 (1968)).

These chemical processes have several disadvantages which include: the cost of the chemical reagents for protection and cleavage; the expense of providing the required low operating temperatures (e.g. −20° C.); the cost of the complex, often multi-step plant; the cost of the measures to contain the toxic chemical reagents (e.g. trimethyl silyl chloride, phosphorous pentachloride and chloroacetyl chloride); and the need to purify the highly impure cephalosporin C (or a derivative) starting material.

There is therefore a need to provide a means of converting cephalosporin C (or a derivative thereof) to 7-ACA (or a corresponding derivative thereof) which is cheap, involves simple technology, is environmentally friendly and is safe. Such criteria are met herein using an enzyme process.

The search for efficient microbiological or enzyme processes for converting cephalosporin C (or a derivative thereof) into 7-ACA (or a corresponding derivative thereof) has been largely unsuccessful. There have been reports in the literature of two-stage enzymatic processes for converting cephalosporin C to 7-ACA. These require the initial conversion of cephalosporin C into glutaryl-7-ACA using a D-amino acid oxidase (see for instance U.S. Pat. Nos. 3,658,649 or 3,801,458) followed by cleavage of the glutaryl side chain to give 7-ACA- Two-stage enzymatic processes have, for example, been described by Shibuya et al, Agric. Biol. Chem.,45, 1561–1567 (1981), but all suffer from the disadvantage of reduced efficiency and increased complexity compared with the one step conversion.

There have also been reports of low activity single-step enzyme reactions. For example, EP0283218, EP0322032, and EP0405846, describe one step conversion of cephalosporin C to 7-ACA using enzymes derived from *Arthrobacter viscosus, Bacillus Megaterium*, and another Bacillus species respectively. EP0474652 describes an enzyme capable of a one step conversion of cephalosporin C to 7-ACA which is derived from *Pseudomonas diminuta*. Despite extensive work in this area it has not been demonstrated that an enzyme isolate as described above is able to be used for production of commercially relevant amounts of 7-ACA.

It is particularly unexpected therefore, that we have isolated a strain of *Pseudomonas vesicularis* which produces an amidohydrolase (also known as amidase or acylase) enzyme that can convert cephalosporin C (or a derivative thereof) into 7-ACA (or a corresponding derivative thereof) by way of a one step conversion. The enzyme activity is only weakly observed in the wild type strain, however, useful activity is achieved following partial purification of the enzyme. Furthermore, the gene coding for the amidohydrolase enzyme activity has also been isolated and sequenced (SEQ ID NO: 1) and can therefore be expressed in a recombinant host such as *E. coli* to produce increased amounts of the enzyme. In addition it is a further feature of this invention that the amidohydrolase enzyme isolated is sufficiently robust that it may be immobilised whilst maintaining significant enzymatic activity. Immobilisation of the enzyme is a particularly important step in the adaption of an enzyme for use within large scale fermentation synthesis of 7-ACA. The use of an immobilised enzyme as compared to free enzyme in fermentation has obvious benefits in significantly reducing the requirement for enzyme and subsequent reduction in cost of 7-ACA manufacture.

Accordingly, there is provided in a first aspect of the present invention a process for the one step conversion of cephalosporin C or a derivative thereof into 7-aminocephalosporanic acid or a corresponding derivative thereof, comprising treating said cephalosporin C or a derivative thereof with cephalosporin C amidohydrolase derived from *Pseudomonas vesicularis* B965, or from any cephalosporin C amidohydrolase producing or potentially producing descendants thereof or from any expression of DNA, particularly a recombinant DNA molecule containing DNA of said *Pseudomonas vesicularis* B965, or any cephalosporin C amidohydrolase producing or potentially producing descendants thereof.

In an alternative aspect of the present invention, there is provided a process for the one step conversion of cephalosporin C or a derivative thereof of formula (I)

wherein
R$^1$ represents a group selected from —CO(CH$_2$)$_3$CH(NHR$^5$)CO$_2$R$^4$, —CO(CH$_2$)$_3$CO$_2$R$^4$ or —CO(CH$_2$)$_2$CO$_2$R$^4$;

R² represents a carboxylic acid or a carboxylate group or a salt, an ester or a protected derivative thereof;

R³ represents a hydrogen atom or a group selected from —CH₂OC(O)CH₃, —CH₂OH, —CH₃, —CH₂OC(O)NH₂ or a pyridiniummethyl group;

R⁴ represents a hydrogen atom or a carboxyl protecting group; and

R⁵ represents a hydrogen atom, a benzoyl group or an amino protecting group;

into 7-aminocephalosporanic acid or a corresponding derivative thereof of formula (II)

(II)

wherein R² and R³ are as defined above;

comprising treating a compound of formula (I) with a cephalosporin C amidohydrolase derived from *Pseudomonas vesicularis* B965, or from any cephalosporin C amidohydrolase producing or potentially producing descendants thereof or from any expression of DNA, particularly a recombinant DNA molecule containing DNA, of said *Pseudomonas vesicularis* B965, or any cephalosporin C amidohydrolase producing or potentially producing descendants thereof.

In preferred aspect of the present invention the compound of formula (I) is cephalosporin C (i.e. R¹ is the group —CO(CH₂)₃CH(NH₂)CO₂H; R² is a carboxylic acid group; and R³ is the group —CH₂OC(O)CH₃) and the compound of formula (II) is 7-aminocephalosporanic acid (i.e. R² is a carboxylic acid group; and R³ is the group —CH₂OC(O)CH₃).

In a further aspect of the present invention, there is provided a recombinant DNA molecule for use in cloning a DNA sequence in a eukaryotic or prokaryotic host, said recombinant DNA molecule comprising a DNA sequence selected from DNA sequences from the DNA sequence set out in SEQ ID NO: 1, which code on expression for a cephalosporin C amidohydrolase enzyme or functional variations of the DNA sequence as depicted in SEQ ID NO: 1, which codes on expression for a cephalosporin C amidohydrolase enzyme.

In a further preferred aspect of the present invention, the DNA or the recombinant DNA comprises a DNA sequence selected from part or all of the DNA sequence set out in SEQ ID NO: 1 or functional variations thereof.

In an alternative aspect of the present invention, there is provided a recombinant DNA molecule for use in cloning a DNA sequence in a eukaryotic or prokaryotic host, said recombinant DNA molecule comprising the DNA sequence as depicted in SEQ ID NO: 1 herein or a functional variation of the DNA sequence as depicted in SEQ ID NO: 1, which codes on expression for a polypeptide having the biological activity of the enzyme cephalosporin C amidohydrolase.

In a further alternative aspect of the present invention, there is provided a recombinant DNA molecule comprising a DNA sequence which hybridizes to the DNA sequence as depicted in SEQ ID NO: 1 or is related to the DNA sequence as depicted in SEQ ID NO: 1 by mutation.

It will be appreciated that the term a "functional variation of the DNA sequence as depicted in SEQ ID NO: 1" as used comprises a DNA sequence selected from:

(i) DNA sequences which are allelic variations of the DNA sequence as depicted in SEQ ID NO: 1, (ii) DNA sequences which hybridize with the above sequences (i) or the DNA sequence as depicted in SEQ ID NO: 1, and (iii) DNA sequences which are degenerate as a result of the genetic code to the above sequences (i) and (ii), or the DNA sequence depicted in SEQ ID NO: 1.

Preferably a "a function variation of the DNA sequence as depicted in SEQ ID NO: 1"will encode a polypeptide which comprises an amino acid sequence substantially corresponding to the sequence of native cephalosporin C amidohydrolase as found in *Pseudomonas vesicularis* B965 SEQ ID NO: 1 or contain one or more deletions, substitutions, insertions, inversions or additions of allelic origin or otherwise. The resulting polypeptide will have at least 80% and preferably 90% homology with the sequence of a native cephalosporin C amidohydrolase enzyme and retain essentially the same cephalosporin C amidohydrolase activity as herein defined or, more preferably, exhibit enhanced activity or enzyme kinetics in the presence of cephalosporin C substrate, for example, by increasing the affinity of the enzyme for its substrate (i.e. reduction in $K_m$) or enhancing the rate of reaction (i.e. increase in $K_{cat}$).

It will be appreciated that the cephalosporin C amidohydrolase-encoding recombinant DNA sequences of the present invention may comprise an operatively linked transcription and translation activating sequence that controls the expression of the cephalosporin C amidohydrolase-encoding recombinant DNA sequence. Such activating sequences for use in recombinant DNA expression are well known in the art.

It will also be appreciated that it is particularly desirable to combine the cephalosporin C amidohydrolase-encoding recombinant DNA sequence with a start codon such as GTG, CTG or, most preferably, ATG, by conventional methods.

Furthermore, the cephalosporin C amidohydrolase-encoding recombinant DNA sequences of the present invention may comprise regulatory signals at the 3' end of the coding sequence such as the stop codons TAG, TAA and TGA, and mRNA polyadenylation and processing signals.

It will be appreciated that a polypeptide with cephalosporin C amidohydrolase activity according to the present invention may be expressed as a fusion protein using a gene fusion where a cephalosporin C amidohydrolase-encoding recombinant DNA sequence of the present invention is joined to a coding sequence for another protein such that their reading frames are in phase. Such gene fusions may be constructed in order to link the polypeptide with cephalosporin C amidohydrolase activity to a signal peptide to allow its secretion by a transformed cell. Another use of this technique may be to enable the splicing of a cephalosporin C amidohydrolase-encoding recombinant DNA sequence behind a promoter sequence in the correct reading frame without the need to position it exactly adjacent to the promoter. A further use of this technique would be to add an affinity tag to the polypeptide with cephalosporin C amidohydrolase activity to facilitate assaying for the polypeptide.

The term "cephalosporin C amidohydrolase-encoding recombinant DNA sequences" is intended to incorporate those sequences which contain one or more modifications such as mutations, including single or multiple base substitutions, deletions, insertions or inversions and which code on expression for a polypeptide possessing cephalosporin C amidohydrolase activity as herein defined. Where modified DNA sequences are used, these may be those recombinant DNA sequences which are degenerate as a result of the genetic code which code on expression for a polypeptide with an amino acid sequence identical to that of a native cephalosporin C amidohydrolase enzyme as found in *Pseudomonas vesicularis* B695.

Alternatively, a cephalosporin C amidohydrolase-encoding recombinant DNA sequence incorporating the modifications described above may code on expression for a polypeptide possessing cephalosporin C amidohydrolase activity as herein defined, in which one or more deletions, substitutions, insertions, inversions or additions of allelic origin or otherwise, results in improved expression of the enzyme and/or the enzyme having improved catalytic activity, for example, by increasing the affinity of the enzyme for its substrate (i.e. reduction in $K_m$) or enhancing the rate of reaction (i.e increase in $K_{cat}$).

It will farther be appreciated that the cephalosporin C amidohydrolase-encoding recombinant DNA sequences of the present invention may be combined with other recombinant DNA sequences.

For example, the cephalosporin C amidohydrolase enzyme of the present invention will accept glutaryl-7-ACA as a substrate, hence the cephalosporin C amidohydrolase-encoding recombinant DNA sequences may be combined with a D-amino acid oxidase-encoding recombinant DNA sequence. Alternatively, the cephalosporin C amidohydrolase enzyme of the present invention naturally accepts cephalosporin C as a substrate, hence the cephalosporin C amidohydrolase-encoding recombinant DNA sequences may be combined with a DAC acetyltransferase-encoding recombinant DNA sequence.

The recombinant DNA sequences of the present invention may be introduced directly into the genome of an antibiotic-producing microorganism in which case they may be used as such. Alternatively, the recombinant DNA sequences of the invention may be introduced by standard techniques known in the art by the use of recombinant DNA expression vectors. When introduced in this way it will be appreciated that the vector will, in general, additionally comprise promoter and/or translation activating sequences, operatively linked to the cephalosporin C amidohydrolase-encoding recombinant DNA sequences and preferably additionally using a selectable marker system for identifying the transformed host, for example, as described herein below.

There is thus provided in a further aspect of the present invention a recombinant DNA expression vector comprising a recombinant DNA sequence of the invention and additionally comprising a promoter and translation activating sequence operatively linked to the cephalosporin C amidohydrolase-encoding recombinant DNA sequence.

In an alternative aspect the recombinant DNA sequences of the present invention may be introduced into a non-antibiotic-producing microorganism, for example, *Escherichia coli*, either directly or as part of a recombinant DNA expression vector to provide the expression and isolation of an enzyme with cephalosporin C amidohydrolase activity which may be useful in catalysing in vitro antibiotic preparation or the in vitro preparation of precursors for use in antibiotic production. Even if expression of a polypeptide with cephalosporin C amidohydrolase activity is not intended in *E. coli*, a suitable recombinant DNA expression vector should preferably be capable of replication in a prokaryotic host such as *E. coli* to facilitate further genetic manipulation.

According to a further aspect of the present invention, there is thus provided a eukaryotic or prokaryotic host transformed with a recombinant DNA expression vector comprising a cephalosporin C amidohydrolase-encoding recombinant DNA sequence of the invention.

Preferred hosts include species of filamentous fungi such as Acremonium spp or Penicillium spp, species of streptomyces, or other bacteria such as *E. coli* or Bacillus spp. Particularly preferred hosts are *Acremonium chrysogenum* or *E. coli*.

In a further aspect of the present invention, there is provided a method of expressing cephalosporin C amidohydrolase activity in a eukaryotic or prokaryotic host comprising:

a) transforming the host cell with a recombinant DNA expression vector that comprises (i) an expression control sequence that functions in the host cell, and (ii) a cephalosporin C amidohydrolase-encoding recombinant DNA sequence which is operatively linked to the expression control sequence;

b) culturing the host cell transformed in step (a) under conditions that allow for expression of cephalosporin C amidohydrolase activity.

It will be appreciated that the recombinant DNA sequence described herein may contain lengths of recombinant DNA which do not code on expression for cephalosporin C amidohydrolase. Although these non-coding sequences in no way detract from the usefulness of the whole recombinant DNA sequence, it may be convenient or desirable to utilise a smaller restriction fragment derived from the recombinant DNA sequences. The restriction fragments may be obtained, for example, by cleavage with suitable restriction endonucleases enzymes or specific exonuclease enzymes by methods well known in the art.

According to yet another aspect of the present invention, there is provided a recombinant DNA expression vector which comprises a gene coding on expression for a cephalosporin C amidohydrolase polypeptide having the amino acid sequence depicted in SEQ ID NO: 1 or allelic or other functionally equivalent variations thereof in which one or more amino acids has or have been added, substituted or removed without substantially affecting the cephalosporin C amidohydrolase activity in the enzyme activity assay described herein.

Suitable recombinant DNA expression vectors may comprise chromosomal, non-chromosomal and synthetic DNA such as derivatives of known bacterial plasmids, for example, 'natural' plasmids such as ColE1 or 'artificial' plasmids such as pBR322, pAT153, pUC18, pUC19, pACYC 184 or pMB9, or yeast plasmids, for example, 2μ.

Other suitable vectors may be phage DNA's, for example, derivatives of M13, or bacteriophage lambda (λ), or yeast vectors such as derivatives of YIp, YEp or YRp.

It will be appreciated that apart from containing the recombinant DNA sequence or a restriction fragment derived therefrom as herein defined, the recombinant DNA expression vector may also comprise a promoter and translational activating sequence which not only functions in the chosen host cell, but also is operatively linked—meaning that it is positioned in the correct orientation and position to control expression of the cephalosporin C amidohydrolase-encoding recombinant DNA sequence. Such an activating sequence may, of course, be found in the full-length recombinant DNA molecule described herein.

Examples of useful promoter sequences which might be used in the recombinant DNA expression vectors of the invention include, for example, the PcbC promoter of isopenicillin N synthetase (IPNS) from Acremonium spp or Penicillium spp, the cefEF promoter of expandase/hydroxylase (DAOCS/DACS) from Acremonium spp, the penDE promoter of Acyl CoA:6APA acyl transferase from Penicillium spp, and numerous promoter sequences from Aspergillus spp including pgk, gpdA, pki, amdS, argB, trpC, alcA, aldD and niaD promoter sequences.

Further examples of useful promoter sequences which might be used in the recombinant DNA expression vectors of the invention include the glycolytic promoters of yeast (for example, the promoter of 3-phosphoglycerate kinase, PGK), the promoters of yeast acid phosphatase (for example, Pho 5) or the alcohol dehydrogenase-2 (alcA) or glucoamylase promoter. Where expression is carried out in a bacterial host such as $E.$ $coli$ useful promoters which might be used in the recombinant DNA expression vectors of the invention are well known in the art, and include the $\lambda P_L/C_I857$ system as well as other common promoters such as tac, lac, trpE and recA. Another suitable expression system would be the T7 polymerase system.

In addition, such recombinant DNA expression vectors may possess various sites for insertion of a cephalosporin C amidohydrolase-encoding recombinant DNA sequence of this invention. These sites are characterised by the specific restriction endonuclease which cleaves them. Such cleavage sites are well recognised by those skilled in the art.

The expression vector, and in particular the site chosen therein for insertion of a selected recombinant DNA fragment and its operative linking to an expression control sequence, is determined by a variety of factors including the number of sites susceptible to a given restriction enzyme, the size of the protein to be expressed, contamination or binding of the protein to be expressed by host cell proteins which may be difficult to remove during purification, the location of start/stop codons, and other factors recognised by those skilled in the art. Thus the choice of a vector and insertion site for a recombinant DNA sequence is determined by a balance of these factors, not all selections being equally effective for a given case. Likewise, not all host/vector combinations will function with equal efficiency in expressing the recombinant DNA sequences of this invention. The selection is made, depending upon a variety of factors including compatability of the host and vector, ease of recovery of the desired protein and/or expression characteristics of the recombinant DNA sequences and the expression control sequences operatively linked to them, or any necessary post-expression modifications of the desired protein.

The recombinant DNA expression vector may also comprise a selectable marker which will facilitate screening of the chosen host for transformants. Suitable markers for use in fungal transformations are well known in the art and include the acetamidase (amdS) gene which confers upon transformants the ability to utilise acetamide as the sole source of nitrogen, antibiotic resistance, for example, the phosphotransferase genes which confer upon transformants resistance to aminoglycosidic antibiotics such as G418, hygromycin B and phleomycin, or resistance to benomyl by transformation with an altered tubulin gene. Another useful marker is the nitrate reductase niaD) gene which confers upon nitrate reductase deficient mutants the ability to utilise nitrate as the sole nitrogen source. Other marker systems for filamentous fungi involve the reversions of arginine auxotrophy using the argB gene, tryptophan C auxotrophy using the trpC gene and uracil auxotrophy using the pyr-4 or pyrG genes.

It will be appreciated that the cephalosporin C amidohydrolase gene of the present invention and the chosen marker gene may conveniently be part of the same plasmid or alternatively they may be on different plasmids in which case the host must be co-transformed using any suitable technique well known in the art.

The recombinant DNA expression vector may also optionally be characterised by an autonomous replication sequence (ars) derived from a fragment of either chromosomal or mitochondrial DNA, preferably from the same species as that being transformed.

In bacterial, e.g. $E.$ $coli$, expression systems, selectable markers are very well established in the art. Of particular use are markers which confer antibiotic resistance to, for example, tetracycline or chloramphenicol.

It will be appreciated that the cephalosporin C amidohydrolase need not necessarily be totally pure, and that a substantial purification by techniques well known in the art should be sufficient to provide an enzyme composition with cephalosporin C amidohydrolase activity.

In a further aspect of the present invention, there is therefore provided a cephalosporin C amidohydrolase-containing enzyme composition capable of the one step conversion of cephalosporin C or a derivative thereof into 7-aminocephalosporanic acid or a corresponding derivative thereof, wherein said enzyme composition is derived from *Pseudomonas vesicularis* B965, or any cephalosporin C amidohydrolase producing or potentially producing descendants thereof, or from any expression of the genetic material of said *Pseudomonas vesicularis* B965, or any cephalosporin C amidohydrolase producing or potentially producing descendants thereof.

Reference herein to protection of amino and carboxyl groups refers to the use of conventional protecting groups, for example as described in "Protective Groups in Organic Synthesis" (2nd Edition) by Theodora Greene and Peter Wuts (John Wiley and Sons Inc. 1991).

The principles of using protecting groups are well established. Greene and Wuts propose a number of criteria for useful protective groups:

It must react selectively in good yield to give a protected substrate that is stable to the projected reactions;

It must be selectively removed in good yield by readily available, preferably non-toxic reagents that do not attack the regenerated functional group;

It should form a crystalline derivative (without the generation of new stereogenic centres) that can easily be separated from side products associated with its formation or cleavage;

It should have a minimum of additional functionality to avoid further sites of reaction.

Suitable protective groups would be readily recognised by a person of ordinary skill in the art.

Salts of the compounds of formulae (I) and (II) include inorganic base salts such as alkali metal salts (e.g. sodium and potassium salts).

Esters of the compounds of formulae (I) and (II) are preferably physiologically acceptable and include acyloxyalkyl esters, for example, lower alkanoyloxymethyl or -ethyl esters such as acetoxymethyl, acetoxyethyl or pivaloyloxymethyl esters, and alkoxycarbonyloxyethyl esters, for example, lower alkoxycarbonyloxyethyl esters such as the ethoxycarbonyloxyethyl ester.

As stated above, the process of the present invention comprises treating cephalosporin C or a derivative thereof with a cephalosporin C amidohydrolase of the present invention. In this context, the term "treating" means any conventional method of contacting the substrate with the enzyme.

Thus, for example, a partially purified solution or cell free broth of crude cephalosporin C or a derivative thereof may be utilised as the feed stream which is treated in a batch-wise or continuous manner with the cephalosporin C amidohydrolase enzyme composition of the present invention. Such a method may be effected with or without any prior purification of the substrate or the enzyme.

Alternatively, the cephalosporin C amidohydrolase of the present invention may be immobilised and used, for example, in a stirred tank reactor or as an enzyme column through which the cephalosporin C or a derivative thereof is passed. Such an immobilised form of the cephalosporin C amidohydrolase enzyme composition constitutes a further aspect of the present invention.

Methods of enzyme immobilisation are well known in the art (see, for instance, "Biotechnology"; Volume 7a, Enzyme Technology (Ed. J F Kennedy), Chapter 7, pp347–404, VCH Publishers, Cambridge, UK, 1987). The enzyme may be bound to a support by, for example covalent, ionic or hydrophobic interactions or alternatively by physical adsorption, for example, by entrapment in gel or fibre, or by microencapsulation.

Suitable support materials include natural polymers such as cellulose, starch, dextran, agarose, alginate and protein; synthetic polymers such as polyacrylamides, polyacrylates and polymethacrylates and styrene dibenzene co-polymers; or minerals such as silica, bentonite, kieselgur, glass and metals.

A particularly preferred means of immobilisation is by covalent binding of the enzyme to a support using activation reagents such as cyanogen bromide or glutaraldehyde, or supports with reactive groups such as oxirane, hydrazine, N-hydroxysuccinimide, carbonyldiimidazole or pyridyldithiopropyl. Particularly preferred supports include cross-linked polyacrylamides, agarose and silica.

Other processes for contacting the substrate with the enzyme include the use of membrane reactors, or by simultaneous culture of *Pseudomonas vesicularis* B965, or any cephalosporin C amidohydrolase producing or potentially producing descendants thereof, with the cephalosporin C (or derivative) producing filamentous fungi.

As used herein, the term "cephalosporin C amidohydrolase producing, or potentially producing, descendants thereof" is intended to incorporate all mutants of *Pseudomonas vesicularis* B965 which might arise through either spontaneous or induced mutation, other than those which do not produce cephalosporin C amidohydrolase. It should be noted however that some non-producers will still be "potentially producing descendants" due to the fact that their genetic material may still be capable of expressing cephalosporin C amidohydrolase as a result of the application of standard recombinant DNA techniques.

Methods of mutagenesis as a means of strain improvement are well known in the art. Modern recombinant DNA techniques provide a more directed means of strain improvement which may involve, for example, the expression of all or part of the genetic material of *Pseudomonas vesicularis* B965 in another microorganism, for example, *E. coli*. The recombinant gene coding on expression for cephalosporin C amidohydrolase may or may not be reintroduced into the parent strain of Pseudomonas. Alternative expression systems well known in the art may be utilised to produce large quantities of cephalosporin C amidohydrolase for use in accordance with the present invention. The expression of all or part of the genetic material of *Pseudomonas vesicularis* B965, or any cephalosporin C amidohydrolase producing or potentially producing descendants thereof constitutes a further aspect of the present invention.

In the following non-limiting examples, included to facilitate further understanding of the present invention, the following abbreviations may be used:

Ceph C—cephalosporin C
7ACA—7-aminocephalosporanic acid
GL-7ACA—7-β-(4-carboxybutanamido)-cephalosporanic acid (glutaryl 7-ACA)
kb—kilobase
DTT—dithiothreitol
EDTA—ethylenediaminetetraacetic acid
MOPS—3-[N-morpholino]propanesulphonic acid
SDS—Sodium lauryl sulphate
SDS PAGE—SDS polyacrylamide gel electrophoresis
Tris-HCl—tris(hydroxymethyl)aminoethane hydrochloride
TSB—tryptone soya broth
DMAB—p-dimethylaminobenzaldehyde
2ME—2-mercaptoethanol
PVDF—polyvinylidene difluoride
gac—GL-7ACA and Ceph C amidohydrolase-encoding gene Preparation 1

Recovery and Assay of Amidohydrolase Enzyme Activity from *Pseudomonas vesicularis*

(a) Natural Isolate Screening System

Microbial isolates were recovered from a wide range of environmental samples using standard microbiological methods as typified in L R Hawker & A H Linton, "Micro-Organisms: Function, Form and Environment", (Edward Arnold Pubs. 1971); R G Board & D W Lovelock, "Sampling-Microbiological Monitoring of Environments", (Academic press, 1973); J M Lynch & N J Poole, "Microbial Ecology: A Conceptual Approach", (Blackwell Scientific, 1979); and "The Oxoid Manual, 5th Edition", (Oxoid Limited, Wade Road, Basingstoke, Hants, RG24 0PW).

Over 105,000 isolates from nature were subjected to an assay system involving around 260,000 assays in the screening for amidohydrolase enzyme activity. For this assay system, the isolates were grown on complex media solidified with agar in order to provide inoculum to an enzyme substrate mixture. During initial screening the enzyme substrate mixture typically contained 100 mM sodium phosphate (pH 7.0); 3 mg/ml Ceph C; 3 mg/ml GL-7ACA; 13.5 mg/ml cloxacillin. A sample of freshly grown cells was incubated for 16–24 hours in enzyme substrate mixture. The 7ACA produced was detected by reaction with DMAB following the method of Balsingham et al (Biochim. Biophys. Acta., 276, 250–256).

From this initial screening, 38 isolates were identified as possessing amidohydrolase activity against GL-7ACA. Further testing was undertaken using the methods of preparation 1(d) and 1(e) described below to identify amidohydrolase activity against Ceph C. Of the 38 isolates with GL-7ACA amidohydrolase activity, only 1 strain (present in 4 sister isolates derived from a single environmental sample) had an amidohydrolase enzyme activity with Ceph C.

(b) Strain B965

The bacteriological characteristics of *Pseudomonas vesicularis* strain B965 are as follows:
1. Morphology
1.1 Colony colour (grown on nutrient agar or TSB agar)— egg yolk yellow, semi-translucent
1.2 Colony morphology—round, regular, entire, convex, smooth, shiny, 0.5 mm diameter after 3 days, 30° C.
1.3 Cell type—rods, 1.5–3 µm length approx
1.4 Gram—negative
1.5 Motility—positive
1.6 Spores—negative
1.7 Growth temperature—optimum 30° C.; 37° C.+; 41° C.–

2. Biochemical Characteristics:

| 2.1 | Reduction of nitrate to nitrite | − |
|---|---|---|
| 2.2 | Reduction of nitrate to nitrogen | − |
| 2.3 | Indole production from tryptophan | − |
| 2.4 | Glucose acidification | − |
| 2.5 | Arginine dihydrolase | − |
| 2.6 | Urease | − |
| 2.7 | β-Glucosidase hydrolysis of aesculin | + |
| 2.8 | Protease hydrolysis of gelatin | − |
| 2.9 | β-Galactosidase activity | − |
| 2.10 | Catalase | + |
| 2.11 | Oxidase | − |
| 2.12 | Production of lysine decarboxylase | − |
| 2.13 | Acid from xylose | − |
| 2.14 | Alkalisation of Simmons citrate | − |
| 2.15 | Reaction in Litmus milk | No Change |
| 2.16 | Assimilation of:- | |
| | glucose | + |
| | arabinose | − |
| | mannose | − |
| | mannitol | − |
| | N-acetyl-glucosamine | − |
| | maltose | − |
| | gluconate | − |
| | caprate | − |
| | adipate | (+) |
| | malate | − |
| | citrate | − |
| | phenyl-acetate | − |
| 2.17 | Cytochrome oxidase | + |

(c) Culture Conditions

The strain is maintained by the sub-culture of single isolated colonies onto agar plates. A number of complex agar media support good growth, in particular tryptone soya broth (TSB; Oxoid CM129) +2.0% w/v agar. This media has a pH of 7.3±0.2 and the following composition:

| Component | g/L |
|---|---|
| Pancreatic digest of caesin | 17.0 |
| Papaic digest of soybean meal | 3.0 |
| Sodium chloride | 5.0 |
| Dibasic potassium phosphate | 2.5 |
| Dextrose | 2.5 |
| Agar powder | 20.0 |

Cells are streaked onto the surface of an agar plate which is incubated at 27.5° C. for 2–6 days. Colonies remain viable for several weeks if the agar plates are stored at 4° C.

For long term preservation a single colony from an agar plate is inoculated into 10 ml of liquid medium. Most complex media designed for bacterial growth are suitable, in particular L-broth can be used. This has the following composition:

| Component | g/L |
|---|---|
| Bacto tryptone (Difco) | 10.0 |
| Yeast extract (Oxoid L21) | 5.0 |
| Sodium chloride | 10.0 |

Inoculated broth is incubated at 27.5° C. with shaking at 220 rpm. After 24 hours the broth is centrifuged. The cell pellet is resuspended in 1 ml of 5% glycerol in water and stored in aliquots at −20° C.

(d) Enzyme Activity Assay

Substrate buffer consists of 5 mM sodium phosphate buffer pH 7.0 containing 13.5 mg/ml cloxacillin and GL-7ACA (3 mg/ml) or cephalosporin C (10 mg/ml). Cell suspensions or semi-purified enzyme samples were incubated in substrate buffer for up to 24 hours at 37° C. At a suitable time a 100 μl sample was withdrawn and mixed with 800 μl 1M citrate-phosphate buffer (pH 4.2). A 100 μl aliquot of fluram reagent was then added, mixed and the sample incubated at room temperature for 1 hour. Fluram reagent consists of fluorescamine (Sigma Chemical Co) at 1 mg/ml in dry acetone. The presence of 7ACA in the reaction mix was detected after derivatisation of the free primary amine group by using fluorescence spectroscopy at an excitation wave length of 378 nm and emission detection at 495 nm in a flow injection assay system with 10% acetone in water as carrier fluid.

In addition, 7ACA production was also demonstrated in an HPLC system. The enzyme reaction mix was derivatised as above and a 20 μl sample applied in a mobile phase consisting of 35% acetonitrile, 0.1% trifluoroacetic acid in HPLC-grade water onto a 15 cm Hypersil ODS 5μ column at 32° C. with a flow rate of 1.5 ml/min. Detection by fluorescence spectroscopy was as above. In this system authentic 7ACA standard has a retention time of 6.7 minutes, with a minor degradation peak at 10.5 minutes.

In typical experiments using these conditions B965 cells sufficient to fill a 10 μl inoculating loop produced 320 μg/ml 7ACA in 18 hours incubation using GL-7ACA as substrate. Using cephalosporin C as substrate with double the volume of cells enabled production of 5 μg/ml 7ACA in an overnight incubation.

(e) Enzyme Recovery

B965 cells were cultured on TSB agar plates essentially by the method of preparation 1(b). The cells were harvested into enzyme buffer, washed and finally resuspended in 10 ml chilled enzyme buffer. Enzyme buffer is 100 mM sodium phosphate buffer (pH 7.0) containing 1 mM DTT and 1 mM benzamidine. The cells were lysed by sonication using a 650W output sonicator (Model W-380, Heat System Ultrasonics Inc, 1938 New Highway, Farmingdale, N.Y. 11735, U.S.A.) on power settings 2–3, 50% cycle, for 12 minutes. The extract was clarified by centrifugation at 18,000 g for 15 minutes at 4° C. The supernatant was recovered, adjusted to 10 ml volume in enzyme buffer, then solid ammonium sulphate was added slowly with gentle mixing at 4° C. to 30% saturation. The solution was clarified by centrifugation as above and the supernatant adjusted to 60% saturation in ammonium sulphate by slow addition of solid as above. The precipitated material was harvested by centrifugation as above and stored over saturated ammonium sulphate.

Further purification of the amidohydrolase was undertaken using an FPLC system (Pharmacia LKB Biotechnology, S-751 82 Uppsala, Sweden) in order to define the properties of the enzyme.

Material recovered from the 30–60% saturation ammonium sulphate precipitate was resuspended in MOPS buffer (10 mM MOPS pH8.0; 1 mM DTT; 1 mM benzamidine). The solution was clarified by brief centrifugation followed by filtration through a 0.2 micron filter. A 5 ml aliquot of enzyme mixture was applied to an HR5/5 MonoQ column pre-equilibrated with MOPS buffer. Amidohydrolase activity was recovered in the eluate between 2–4 ml after loading. This fraction was adjusted to 30% saturation in ammonium sulphate and loaded to an HR10/30 phenylsuperose column. Elution of protein was achieved using a salt gradient regime varying from 30%–0% saturation in ammonium sulphate with a running buffer consisting of 100 mM sodium phosphate pH7.0, 1 mM DTT. Amidohydrolase activity was recovered at between 18.5%–15.0% saturation of ammonium sulphate under these conditions.

Following these purification steps the following typical values of amidohydrolase activity were obtained using the method of preparation 1(c):

| Extract (μl) | Substrate (mg/ml) | Time (hr) | 7 ACA Produced (μg/ml) |
|---|---|---|---|
| 10 | GL-7ACA (2) | 4 | 22 |
| 80 | Ceph C (50) | 8 | 14.5 |

(f) Cephalosporin C Amidohydrolase Enzyme Properties

Physical

1. Apparent molecular weight by gel filtration: 70000±4000.
2. Subunit molecular weight by SDS-PAGE:α30,000,β60,000.
3. Soichiometry apparent: α1β1.
4. Isoelectric point: pI 10.5±0.2.
5. Hydrophobicity: does not bind to butyl-, hexanyl-, octyl- or decyl-derivatised agarose; binds to phenyl-derivatised agarose with elution at 650–800 mM ammonium sulphate.
6. Stable in presence of 1 mM DTT.
7. Precipitates from solution at or above 50% saturation ammonium sulphate.

Kinetic

1. pH optimum: 8 (effective range 7–9).
2. Temperature optimum: 40° C. (stable to 45° C.).
3. $K_m$: GL-7ACA substrate at 1.2–7.2 mM, $K_m$=2–4 mM; Ceph C substrate at 0.5–1.5 mM, $K_m$=0.012 mM; Ceph C substrate at 3.6–132 mM, $K_m$=60–100 mM.
4. Inhibitors: ammonium sulphate >6% w/v.
5. Specific activity maximum 0. 141 μmol 7ACA/min/mg enzyme using Ceph C substrate.

Example Substrates:

| R¹ | R³ | name | Assay response[a] (% rate of 7ACA) |
|---|---|---|---|
| HOOC-(CH2)3-C(=O)- | $CH_2OCOCH_3$ | glutaryl-7ACA | 100[b] |
| HOOC-CH(NH2)-(CH2)2-C(=O)- | $CH_2OH$ | deacetylcephalosporin C | 9.8 |
| HOOC-CH(NH2)-(CH2)2-C(=O)- | $CH_2OCOCH_3$ | cephalosporin C | 8.0 |
| PhC(=O)NH-CH(COOH)-(CH2)2-C(=O)- | $CH_2N^+$-pyridinium | benzoylcephalosporin-3-pyridiniummethyl | 3.5 |

-continued

| R¹ | R³ | name | Assay response[a] (% rate of 7ACA) |
|---|---|---|---|
| ![benzoyl structure] | $CH_2OCOCH_3$ | benzoylcephalosporin C | 2.8 |
| ![succinyl structure] | $CH_2OCOCH_3$ | succinyl-7ACA | 0.8 |

[a]Assay response is given as product yield standardised to the 7ACA produced from GL-7ACA under equivalent reaction conditions. For the comparison it is assumed that products have molar extinction coefficients equivalent to 7ACA, such that the response was calculated directly from product peak area on HPLC. The standard reaction used 100 μl enzyme prepared by the procedure of preparation 2(d) from NM522/pVS44 cells, with 10 mg/ml substrate in overnight reaction at 27° C.
[b]Assay response obtained using 10 μl of above enzyme extract, with 3 mg/ml substrate in 2 hour reaction at 27° C. The actual response was then extrapolated to equivalent conditions to those used with the more slowly hydrolysed substrates.

(a) Assay response is given as product yield standardised to the 7ACA produced from GL-7ACA under equivalent reaction conditions. For the comparison it is assumed that products have molar extinction coefficients equivalent to 7ACA, such that the response was calculated directly from product peak area on HPLC. The standard reaction used 100 μl enzyme prepared by the procedure of preparation 2(d) from NM522/pVS44 cells, with 10 mg/ml substrate in overnight reaction at 27° C.

(b) Assay response obtained using 10 μl of above enzyme extract, with 3 mg/ml substrate in 2 hour reaction at 27° C. The actual response was then extrapolated to equivalent conditions to those used with the more slowly hydrolysed substrates.

Preparation 2

Cloning and Identification of Amidohydrolase-Encoding Gene (a) Isolation of *P. vesicularis* Genomic DNA The organism was grown to late-log phase in 100 ml L-broth at 28° C. The cells were pelleted by centrifugation (4000 g, 10 minutes) and resuspended in 5 ml of TNES buffer (200 mM Tris-HCl (pH 8.5); 250 mM EDTA; 0.5% SDS). After 1 hour at 37° C., proteinase K was added to 50 μg/ml and incubation continued at 37° C. for 1 hour. An equal volume of phenol/chloroform/isoamyl alcohol (50:49:1), saturated with TNES buffer, were added and the suspension vortexed for 15 seconds. After 10 minutes, at room temperature, the phases were separated by centrifugation (15,000 g, 10 minutes 20° C.). Two volumes of absolute ethanol was slowly added to the supernatant, and high molecular weight DNA spooled on to a glass rod. The DNA was dissolved in TE buffer (10 mM Tris-HCl, 1 mM EDTA, pH 8.0).

(b) Construction of the *P. vesicularis* Gene Library

Approximately 150 μg *P. vesicularis* DNA was digested in a 900 μl reaction for 45 minutes with 5 units Sau3AI. The DNA was precipitated using ethanol, resuspended in 500 μl buffer and loaded on to a 38 ml 10–40% sucrose gradient made in 1M NaCl, 20 mM Tris-HCl (pH8.0), 5 mM EDTA. After centrifugation overnight (26000 rpm in SW28 rotor, Beckman L8-M ultracentrifuge, 15° C.) 500 μl fractions were taken, the DNA ethanol precipitated, and analysed by agarose gel electrophoresis. Fractions in the size range 5–12 kb were retained.

Approximately 200 ng dephosphorylated BamHI-digested pSU18 vector was prepared by standard techniques. Plasmid pSU18 was obtained from Dr F de la Cruz (Departmento de Biologio Molecular, Universidad de Cantabria, 39001 Santander, Spain) and is derived from pSU2713 (Martinez et al, Gene, 68 (1988) p159–162). The prepared vector was ligated with approximately 500 ng size fractionated *P. vesicularis* DNA. Ligation was performed at 14° C. overnight in a volume of 20 μl with 1U T4 DNA ligase. The ligation mix was transformed into the widely available *E. coli* strain NM522. Transformants were selected on L agar plus chloramphenicol (30 μg/ml).

(c) Identification of Amidohydrolase-Encoding Clones

Single colonies were spread onto L agar plates containing chloramphenicol at 30 μg/ml and grown at 27.5° C. for 2–4 days. Aliquots of culture were recovered using a 10 μl inoculating loop then resuspended in 0.5 ml substrate buffer and further treated following the procedure of preparation 1(c). Isolates with amidohydrolase activity can be identified by these means.

(d) Amidohydrolase Activity of Clones

A clone identified by the method of preparation 2(c) carries an active gac gene on a recombinant plasmid. A further derivative plasmid was constructed by the subcloning of a 8.1 kb PstI fragment carrying the gac gene into pSU18 by standard methods. This plasmid is termed pVS42. A restriction map of the *P. vesicularis* DNA portion of pVS42 is illustrated in FIG. 1(a). Amidohydrolase activity using GL-7ACA or cephalosporin C as substrate is approximately equivalent between *E. coli*/pVS42 and the original *P. vesicularis* isolate using whole cells by the method of preparation 1(c).

*E. coli* B1113 was grown on TSB agar plates following the method of preparation 1(b). The confluent cell growth was processed for amidohydrolase recovery essentially following the procedure of preparation 1(d) to the cell-free extract stage.

Amidohydrolase activity was further purified by application of the cell-free extract to a DE52 cellulose column (Whatman Ltd, Maidstone, Kent ME14 2LE). The majority of proteins in the extract bind to the matrix and amidohydrolase activity is not retained.

Following this purification step the following typical values of amidohydrolase activity were obtained using the method of preparation 1(c).

| Extract | Substrate (mg/ml) | Time (hr) | 7ACA Produced (µg/ml) |
|---|---|---|---|
| 50 | GL-7ACA (3) | 3 | 102 |
| 50 | Ceph C (10) | 4 | 4.5 |

Further subclones were derived from pVS42 by partial digestion of pVS42 plasmid DNA with the restriction enzyme KpnI, ligation of the resultant mixture of reaction products and transformation into *E. coli* strain NM522 using standard methods. Screening of the resultant isolates using procedures of preparation 1(b) and 1(c) identified a number of clones with enhanced cephalosporin C amidohydrolase activity. One such isolate was found to contain a plasmid, termed pVS44. A restriction map of the *P. vesicularis* DNA portion of pVS44 is illustrated in FIG. 1(b).

Cephalosporin C amidohydrolase enzyme activity was recovered from NM522/pVS44 cells using procedures of preparation 1(b) and 1(c) to the cell free extract stage followed by chromatography on DE52 cellulose as described above. In a typical assay using the method of preparation 1(c), a 10 µl extract produced 12 µg/ml 7ACA from 50 mg/ml cephalosporin C in a 3 hour incubation at 27° C. This represents approximately 30-fold improvement over the level of activity obtained using B 1113 strain extract at an equivalent stage of purification.

(e) Additional Subcloning to Improve Amidohydrolase Activity

Figure 1:
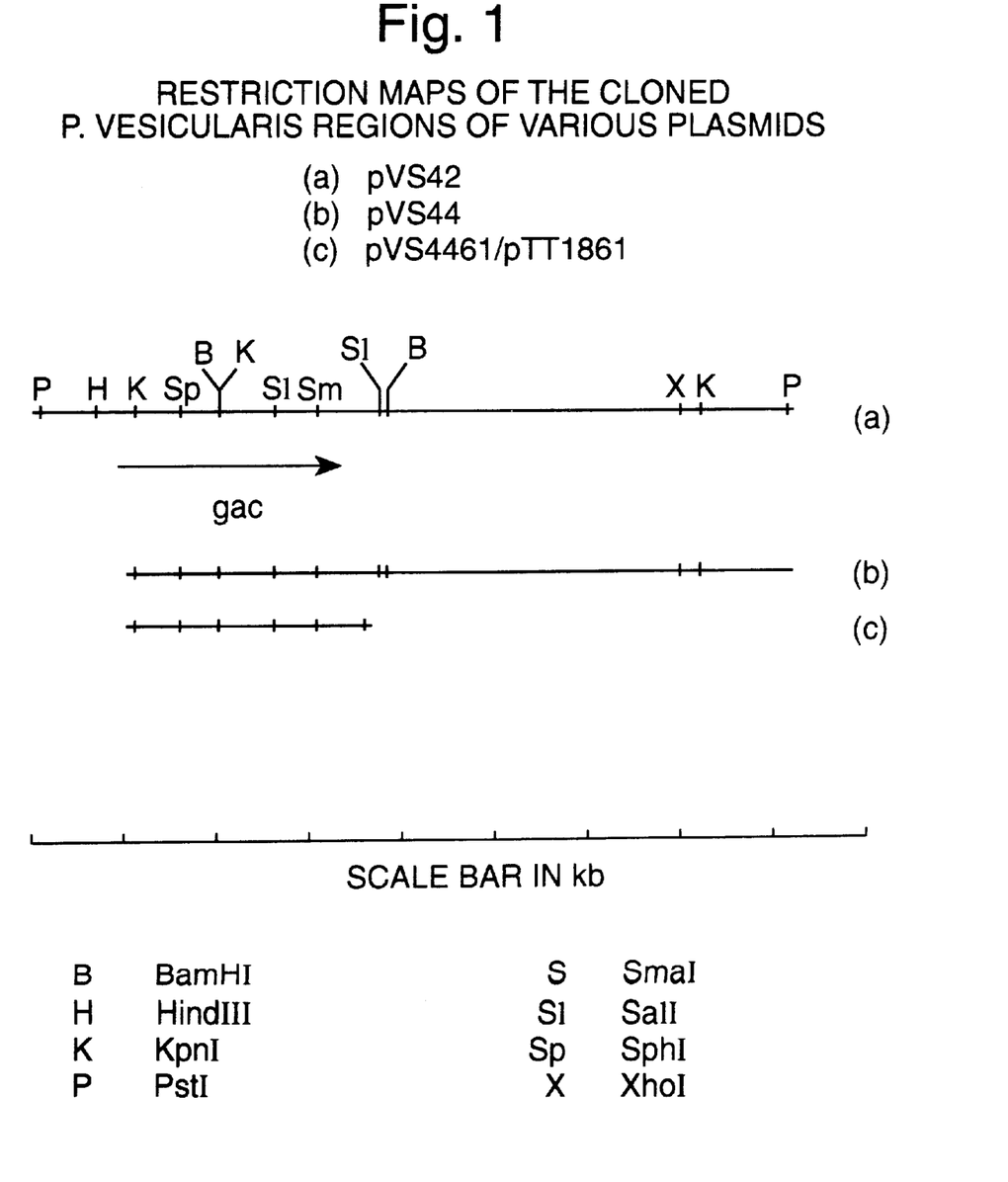
FIG. 1. Restriction maps of the cloned *P. Vesicularis* regions of various plasmids (a) pVS42 (b) pVS44 and (c) pVSA4416/pTT 1861.

The size of the *P. vesicularis*-derived DNA fragment encoding the active gac of pVS44 was reduced by progressive exonuclease III enzyme digestion. The methodology was as described by Henikoff ("Methods in Enzymology", 155 (1987) 156–165). Unidirectional deletion into the *P. vesicularis* DNA portion of pVS44 was initiated at the XhoI site, while the pSU18 DNA portion was protected from exonuclease III attack by cutting at the PstI site forming the boundary between the *P. vesicularis* and *E. coli*-derived DNAs. These sites are indicated in FIG. 1. Following enzyme treatments and self-ligation of reaction products using the methods of Henikoff (loc. cit.), transformation of *E. coli* produced a population of colonies carrying variant plasmids with deletions of differing sizes. The population was screened for amidohydrolase activity by the method of preparation 1(c). A whole cell assay was used for screening. A 10 µl inoculation loop full of cells grown for 2 days at 27.5° C. was suspended in 1 ml substrate buffer (10 mg/ml cephalosporin C) and incubated overnight at 37° C. One of the isolates recovered from this screen with increased amidohydrolase activity carried the plasmid pVS4461. The *P. vesicularis*-derived portion of pVS4461 is illustrated in FIG. 1(c).

The *P. vesicularis* portion of pVS4461 was recovered as a EcoRI-HindIII fragment using restriction sites derived from the pSU18 multiple cloning region into which the *P. vesicularis* DNA was originally inserted. This EcoRI-HindIII fragment (of about 2.8 kb) was cloned between the EcoRI and HindIII sites of the commercially available phagemid vector pTZ18R (Pharmacia P-L Biochemicals Inc, Milwaukee, Wis. 53202, USA) to yield the phagemid termed pTZ1861. DNA of pTZ1861 was cut at the single ScaI site within the β-lactamase gene. A plasmid derivative of the widely available vector pACYC184 was used as the source of a DNA fragment encoding the tetracycline resistance gene. This fragment was converted to blunt ends, isolated and ligated to ScaI-cut, diphosphorylated pTZ1861 DNA following standard methods. Following transformation isolates selected on the basis of tetracycline resistance were screened for amidohydrolase activity. One such active tetracycline-resistant isolate was selected and the recovered phagemid termed pTT1861. The *P. vesicularis* derived portion of pTT1861 is identical to that in pVS4461 and is illustrated in FIG. 1(c).

*E. coli* strains carrying the various amidohydrolase plasmids were screened for amidohydrolase activity by the method of preparation 1(c) using a 10 µl inoculation loop full of well grown cells, suspended in substrate buffer containing 50 mg/ml Ceph C.

Ceph C amidohydrolase activity was assessed following 3 hours incubation at 27.5° C. In comparative testing the relative activities of isolates carrying the plasmids and phagemids described are as follows:

| Plasmid/Phagemid | Relative Amidohydrolase Activity |
|---|---|
| pVS42 | 1 |
| pVS44 | 20–30 |
| pVS4461 | 60–90 |
| pTT1861 | 160–240 |

(f) Amidohydrolase Gene Sequence

The DNA sequence of the gac gene was derived by standard dideoxynucleotide incorporation methods. DNAs of the plasmids pVS42, pVS44 and subclones thereof were used as templates for sequencing reactions. Sequencing was initiated from either commercially available oligonucleotide primers annealing to the lacZ' portion of the plasmids or from oligonucleotides designed to anneal within the gac gene. Double stranded DNA was purified using Sephacryl S-400 Spun Columns following the manufacturer's instructions (Pharmacia P-L Biochemicals), then mixed with primer and treated with ⅕ vol 1N NaOH at 37° C. for 10 minutes. The preparations were neutralised with 1N HCl and used in sequencing reactions following standard methodology (Sequenase Version 2.0 Kit; US Biochemical Corp). Some highly GC-rich regions caused the appearance of sequencing artefacts through sequence compressions or premature reaction termination. These were resolved through a combination of using deoxyinosine triphosphate in place of deoxyguanosine triphosphate and additional reaction of sequencing products with terminal deoxynucleotidyl transferase prior to resolution by PAGE, following the manufacturer's recommended procedures (US Biochemical Corp) and the method of Fawcett and Bartlett (BioTechniques, 9, 46–49 (1990)). Some of the sequence was derived from deletion subclones. The deletions were constructed using exonuclease III digestion following the methods of Henikoff (loc. cit.). The derived DNA sequence and deduced amino acid sequence thereof are shown in SEQ ID NO: 1.

(g) Amidohydrolase Amino Acid Sequence

The amidohydrolase enzyme specified by the gac gene encoded by the pTT1861 plasmid was purified to homogeneity for amino acid sequence analysis. The E. coli strain NM522/pTT1861 was grown on TSB medium supplemented with 10 μg/ml tetracycline and solidified with 1.5% w/v agar. Growth was for 18hours at 37° C. About 1 g cell paste recovered by scraping from the agar surface was washed and resuspended in 4 ml ice cold lysis buffer (10 mM MOPS pH 8.0; 1 mM DTT; 1 mM benzamidine). Cells were lysed by sonication (650W output sonicator for 4 pulses of 2 minutes at power setting 2; sample chilled on ice). The lysate was clarified by centrifugation at 15,000 rpm for 30 minutes. Enzyme purification was achieved using a Pharmacia FPLC system. The clarified lysate containing about 100 mg soluble protein was applied to an 5/5 MonoQ ion exchange column pre-equilibrated with lysis buffer. Amidohydrolase activity was recovered in eluate fractions between 2–4 ml after loading. This material was adjusted to 30% saturation in ammonium sulphate and applied to an HR10/30 phenylsuperose hydrophobic interaction column. Elution of protein was achieved using a non-linear gradient varying from 30%–0% saturation in ammonium sulphate in a 10 mM sodium phosphate buffer containing 1 mM DTT. Eluate fractions containing amidohydrolase activity were pooled and applied to an HR10/30 Superose 12 gel filtration column in the phosphate buffer. Amidohydrolase activity was recovered in fractions equivalent to protein of molecular weight 70,000±4000. At this stage, 3 protein bands were present following SDS-PAGE (Pharmacia Phastsystem). The eluate fractions containing amidohydrolase activity were concentrated using a centrifugal membrane filter device (Centricon 30 Microconcentrator, Amicon Division of W R Grace, Danvers Mass. 01923, USA). About 3 mg protein was recovered by this procedure. Aliquots of protein were treated with SDS and 2ME and resolved by SDS-PAGE using ultrapure reagents following standard methods as described by Hames and Rickwood in "Gel Electrophoresis of Proteins: A Practical Approach" (IRL Press). Major peptide species of about 30,000 and 60,000 molecular weights were recovered by blotting to PVDF membrane (P Matsudaira, J Biol Chem., 262, 10035–10038 (1987)). The material was subjected to automated amino acid analysis by Edman degradation in an Applied Biosystems 477A Protein Sequencer (Applied Biosystems Inc., FosterCity, Calif. 94404, USA).

The following N-terminal amino acid sequences were derived:

α-peptide (30,000 molecular weight):

Thr Ile Gly Asn Ser Ser SerNal Pro Ala Thr Ala Pro Thr -?- Val Ala Gly Leu Ser Ala Pro Ile

β peptide (60,000 molecular weight):

Ser Asn Ala Trp Thr Val Ala Gly Ser Arg Thr Ser Thr Gly -?- Pro Ile Leu Ala Asn Asp Pro His Leu

These sequences are identified and located in SEQ ID NO: 1. The α-peptide sequence identified by amino acid sequencing represents a fusion protein between the N-terminus of the lacZ α-peptide derived from the plasmid vector pTT1861 and an internal portion of the α-peptide sequence derived from the P. vesicularis gac gene. The precise linkage of the lacZ-gac fusion is detailed in FIG. 3. The linkage brings the two peptide sequences together as a precise in-frame fusion at the KpnI site of the DNA sequence. As this KpnI site forms the boundary of the gac gene in the sequence, it follows that from the methods of construction outlined in Preparation 2(d) and 2(e), the construct pVS44 and all derivatives including pVS4461 and pTT1861 represent similar lacZ-gac fusions. Expression of amidohydrolase activity in all such constructs utilises a recombinant system, rather than the natural P. vesicularis gac promoter.

Preparation 3

Immobilisation of Amidohydrolase (a) Amidohydrolase Purification

E. coli strain NM522/pVS44 was grown on TSB medium supplemented with 10 μg/ml chloramphenicol and solidified with 1.5% w/v agar. Growth was for 2 days at 27.5° C. Cell paste was recovered by scraping from the agar surface, resuspended and washed in lysis buffer (10 mM MOPS pH 8.0; 1 mM DTT; 1 mM benzamidine). About 65 g cell paste was lysed in 350 ml ice cold buffer by sonication (650W output, power setting 4, 5 passes through a continuous flow head at 35 ml/min flow, sample chilled on ice). The lysate was clarified by centrifugation (15,000 rpm, 30 min) to yield 3120 mg soluble protein. This material was passed over a 300 ml column of pre-equilibrated DE52 cellulose. Fractions eluting between 100 ml–500 ml after loading contained amidohydrolase activity in a total of 398 mg protein. The protein was concentrated using a centrifugal membrane device (Centriprep 30 concentrator, Amicon).

(b) Enzyme Immobilisation

The concentrated extract (300 mg protein, 12.54 ml) was adjusted to 100 mM phosphate buffer pH 8.0: 1 mM DTT; 1 mM benzamidine, and mixed with 3.0 g (dry weight) oxirane-linked polyacrylic matrix (Eupergit C: Rohm Pharma GmbH, D-6100 Darmstadt Germany). Immobilisation, monitored by protein removal from the liquid phase, was complete by 116 hours. About 120 mg protein became covalently linked to the support. Excess protein was removed by washing in the phosphate buffer.

(c) Immobilised Enzyme Activity

Immobilised amidohydrolase activity was monitored by allowing the enzyme catalysed reaction to occur using an automated control system set to detect and maintain the reaction pH at a set point (a pH stat system). A pH monitor was set such that a fall in pH from the set point triggered a peristaltic pump to allow regulated dosing of alkali titrant.

A reaction volume of 50 ml contained 50 mg/ml substrate (GL-7ACA or Ceph C) in water maintained at 25° C. The reaction mix was adjusted to pH 8.0 using 2M NaOH as titrant before addition of about 3 g dry weight (12 g wet weight) immobilised enzyme to initiate the reaction. The suspension was stirred using an overhead paddle type stirrer. Reaction progress was monitored by titrant addition rate and sampling at intervals. The samples were assayed for 7ACA by the DMAB method as in preparation 1(a). By this method the following activities were measured:

|            | Activity                                          |                                                 |
| ---------- | ------------------------------------------------- | ----------------------------------------------- |
| Substrate  | μmole 7ACA/min/g dry weight immobilised enzyme    | μmole/min/g wet weight immobilised enzyme       |
| Ceph C     | 0.95                                              | 0.24                                            |
| GL-7ACA    | 4.7                                               | 1.2                                             |

The maximum conversion with cephalosporin C (22 hours) was 1.7%, with GL-7ACA as substrate a conversion of 9.0% was achieved.

We claim:

1. A process for the one step conversion of cephalosporin C or a derivative thereof into 7-aminocephalosporanic acid or a corresponding derivative thereof, comprising treating said cephalosporin C or a derivative thereof with cephalosporin C amidohydrolase derived from *Pseudomonas Vesicularis* B965, or from any cephalosporin C amidohydrolase producing descendants thereof.

2. A process for the one step conversion of cephalosporin C or a derivative thereof into 7-aminocephalosporanic acid or a corresponding derivative thereof, comprising treating said cephalosporin C or a derivative thereof with cephalosporin C amidohydrolase enzyme derived from expression of DNA of *Pseudomonas Vesicularis* B965, or any cephalosporin C amidohydrolase producing descendants thereof.

3. A process for the one step conversion of cephalosporin C or a derivative thereof into 7-aminocephalosporanic acid or a corresponding derivative thereof, comprising treating said cephalosporin C or a derivative thereof with cephalosporin C amidohydrolase derived from expression of DNA comprising of part or all of the DNA sequence in SEQ ID NO:1; or a DNA sequence degenerate as a result of the genetic code or allelic variations thereof.

4. A process as claimed in claim 2 or 3 wherein cephalosporin C amidohydrolase is derived from expression of a recombinant DNA molecule comprising part or all of the sequence in SEQ ID NO:1 ; or a DNA sequence degenerate as a result of the genetic code or alielic variations thereof.

5. A process as claimed in claim 1 wherein cephalosporin C amidohydrolase is immobilised.

6. Cephalosporin C amidohydrolase derived from *Pseudomonas Vesicularis* B965 in a substantially pure form.

7. Cephalosporin C amidohydrolase as claimed in claim 6 wherein said cephalosporin C amidohydrolase is immobilized.

8. A process for the preparation of 7-aminocephalosporanic acid from cephalosporin C comprising treating said cephalosporin C with said cephalosporin C aminohydrolase according to claim 6 under conditions such that said 7-aminocephalosporanic acid is produced.

* * * * *